United States Patent
Phan

(10) Patent No.: US 9,591,456 B2
(45) Date of Patent: Mar. 7, 2017

(54) TRIGGERING GEOLOCATION FIX ACQUISITIONS ON TRANSITIONS BETWEEN PHYSICAL STATES

(71) Applicant: Samsung Electronics Co., Ltd., Suwon-si, Gyeonggi-do (KR)

(72) Inventor: Thomas Phan, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/332,177

(22) Filed: Jul. 15, 2014

(65) Prior Publication Data

US 2015/0018014 A1    Jan. 15, 2015

Related U.S. Application Data

(60) Provisional application No. 61/846,463, filed on Jul. 15, 2013.

(51) Int. Cl.
| | |
|---|---|
| *H04W 24/00* | (2009.01) |
| *H04W 4/02* | (2009.01) |
| *G01P 13/00* | (2006.01) |
| *A61B 5/11* | (2006.01) |
| *A61B 5/00* | (2006.01) |

(52) U.S. Cl.
CPC ............ *H04W 4/027* (2013.01); *G01P 13/00* (2013.01); *H04W 4/028* (2013.01); *A61B 5/1123* (2013.01); *A61B 5/6898* (2013.01)

(58) Field of Classification Search
CPC ......... H04W 4/00; H04W 4/02; H04W 4/027; H04W 4/028; H04W 4/021; H04W 4/025; H04W 4/04; H04W 4/16; H04W 64/00; H04W 64/04

USPC ........... 455/403, 404.1, 404.2, 456.1, 456.2, 455/456.3, 456.5, 456.6
See application file for complete search history.

(56) References Cited

U.S. PATENT DOCUMENTS

| | | | |
|---|---|---|---|
| 7,429,914 B2 * | 9/2008 | Carlson ..................... | G01S 5/06 340/286.01 |
| 8,204,684 B2 | 6/2012 | Forstall et al. | |
| 8,369,264 B2 | 2/2013 | Brachet et al. | |
| 2009/0005061 A1 | 1/2009 | Ward et al. | |
| 2010/0304754 A1 | 12/2010 | Czompo et al. | |
| 2011/0070863 A1 | 3/2011 | Ma et al. | |
| 2011/0140956 A1 * | 6/2011 | Henry et al. ............... | 342/357.3 |
| 2011/0215903 A1 | 9/2011 | Yang et al. | |

(Continued)

OTHER PUBLICATIONS

Wang, Y. et al., "A Framework of Energy Efficient Mobile Sensing for Automatic User State Recognition", Proceedings of the 7th International Conference on Mobile Systems, Applications, and Services (MobiSys'09), Jun. 22, 2009, pp. 179-192, ACM, United States.

(Continued)

*Primary Examiner* — Jean Gelin
(74) *Attorney, Agent, or Firm* — Sherman IP LLP; Kenneth L. Sherman; Steven Laut

(57) ABSTRACT

A method and device for triggering acquisition of geolocation fix information. The method include determining activity state information based on information from one or more sensors. It is determined if an activity state has transitioned to a particular activity state based on the activity state information. Geolocation fix information is acquired if the activity state transitioned to the particular activity state.

30 Claims, 12 Drawing Sheets

(56) References Cited

U.S. PATENT DOCUMENTS

| | | | |
|---|---|---|---|
| 2011/0231483 | A1 | 9/2011 | Derraugh et al. |
| 2011/0241827 | A1 | 10/2011 | Varoglu |
| 2011/0306304 | A1 | 12/2011 | Forutanpour et al. |
| 2012/0083705 | A1* | 4/2012 | Yuen et al. .................. 600/508 |
| 2013/0122928 | A1* | 5/2013 | Pfluger .................. G01P 13/00 455/456.1 |
| 2013/0138389 | A1* | 5/2013 | Gyongy ................ A61B 5/1118 702/141 |
| 2013/0196670 | A1 | 8/2013 | Kim et al. |
| 2013/0238700 | A1 | 9/2013 | Papakipos et al. |
| 2013/0238921 | A1 | 9/2013 | Alpert et al. |
| 2013/0281115 | A1* | 10/2013 | Dupray et al. ............. 455/456.1 |
| 2015/0154868 | A1* | 6/2015 | Neuner et al. ............. 455/456.1 |
| 2015/0168174 | A1* | 6/2015 | Abramson et al. ........ 455/456.2 |

OTHER PUBLICATIONS

Shafer, I. et al., "Movement Detection for Power-Efficient Smartphone WLAN Localization", Proceedings of the 13th ACM International Conference on Modeling, Analysis, and Simulation of Wireless and Mobile Systems (MSWIM'10), Oct. 17-21, 2010, p. 81-90, ACM, United States.

Reddy, S. et al., "Using Mobile Phones to Determine Transportation Modes", Journal of ACM Transactions on Sensor Networks, Feb. 2010, pp. 1-27, vol. 6, No. 2, Article 13, ACM, United States.

Ravi, N. et al., "Activity Recognition from Accelerometer Data", Proceedings of the 17th Conference on Innovative Applications of artificial Intelligence—vol. 3 (IAAA'05), Jul. 9, 2005, pp. 1541-1546, AAAI Press, ACM, United States.

Phan, T., "Generating Natural-Language Narratives from Activity Recognition with Spurious Classification Pruning", Proceedings of the Third International Workshop on Sensing Applications on Mobile Phones (PhoneSense'12), Nov. 6, 2012, pp. 1-5, ACM, United States.

Oshin, T.O. et al., "Improving the Energy-Efficiency of GPS based Location Sensing Smartphone Applications", Proceedings of the 11th International Conference on Trust, Security and Privacy in Computing and Communications (TustCom), Jun. 25-27, 2012, pp. 1698-1705, IEEE, United States.

Nath, S., "ACE: Exploiting Correlation for Energy-Efficient and Continuous Context Sensing", Proceedings of the 10th International Conference on Mobile Systems, Applications and Services (MobiSys'12), Jun. 25, 2012, pp. 29-42, ACM, United States.

Miluzzo, E. et al., "Sensing Meets Mobile Social Networks: The Design, Implementation and Evaluation of the CenceMe Application", Proceedings of the 6th ACM conference on Embedded Network Sensor Systems (SenSys'08), Nov. 5, 2008, pp. 337-350, ACM, United States.

Lester, J. et al., "A Practical Approach to Recognizing Physical Activities", Proceedings of the 4th International Conference on Pervasive Computing (Pervasive'06), May 7, 2006, pp. 1-16, ACM, United States.

Kwapisz, J.R. et al., "Activity Recognition using Cell Phone Accelerometers", ACM SIGKDD Explorations Newsletter, Mar. 31, 2011, pp. 74-82, vol. 12, Issue 2, ACM, United States.

Kjaergaard, M.B. et al., "EnTracked: Energy-Efficient Robust Position Tracking for Mobile Devices", Proceedings of the 7th International Conference on Mobile Systems, Applications, and Services (MobiSys'09), Jun. 22, 2009, pp. 221-234, ACM, United States.

Kim, D.H. et al., "SensLoc: Sensing Everyday Places and Paths using Less Energy", Proceedings of the 8th ACM Conference on Embedded Networked Sensor Systems (SenSys'10), Nov. 3, 2010, pp. 43-56, ACM, United States.

Huynh, T. et al., "Scalable Recognition of Daily Activities with Wearable Sensors", Scalable Recognition of Daily Activities with Wearable Sensors, Proceedings of the Third International Symposium LoCA 2007, Sep. 12-20, 2007, pp. 50-67, Springer, United States.

Constandache, I. et al., "EnLoc: Energy-Efficient Localization for Mobile Phones", INFOCOM 2009, Apr. 19-25, 2009, pp. 2716-2720, IEEE, United States.

Bao, L. et al., "Activity Recognition from User-Annotated Acceleration Data", Pervasive Computing, Proceedings of the Second International Conference Pervasive 2004, Apr. 21-23, 2004, pp. 1-17, Springer, United States.

Zhuang, Z. et al., "Improving Energy Efficiency of Location Sensing on Smartphones", Proceedings of the 8th International Conference on Mobile Systems, Applications, and Services (MobiSys'10), Jun. 15, 2010, pp. 315-330, ACM, United States.

Pathak, A. et al., "Where is the energy spent inside my app? Fine Grained Energy Accounting on Smartphones with Eprof", Proceedings 7th ACM European Conference on Computer Systems (EuroSys'12), Apr. 10, 2012, pp. 29-42, ACM, United States.

Lu, H. et al., "The Jigsaw Continuous Sensing Engine for Mobile Phone Applications", Proceedings of the 8th ACM Conference on Embedded Networked Sensor Systems (SenSys'10), Nov. 3, 2010, pp. 71-84, ACM, United States.

Liu, J. et al., "Energy Efficient GPS Sensing with Cloud Offloading", Proceedings of the 10th ACM Conference on Embedded Network Sensor Systems (SenSys'12), Nov. 6, 2012, pp. 85-98, ACM, United States.

Lin, K. et al., "Energy-Accuracy Trade-off for Continuous Mobile Device Location", Proceedings of the 8th International Conference on Mobile Systems, Applications, and Services (MobiSys'10), Jun. 15, 2010, pp. 285-298, ACM, United States.

Abdesslem, F.B. et al., "Less is More: Energy-Efficient Mobile Sensing with SenseLess", Proceedings of the 1st ACM Workshop on Networking, Systems, and Applications for Mobile handhelds (MobiHeld'09), Aug. 19, 2009, pp. 61-62, ACM, United States.

Phan, T., "Intelligent Energy-Efficient Triggering of Geolocation Fix Acquisitions Based on Transitions Between Activity Recognition States", Proceedings of the 5th International Conference (MobiCASE'13), Nov. 7-8, 2013, pp. 104-121, Springer, United States.

State, B. et al., "Stuyding Inter-National Mobility through IP Geolocation", Proceedings of the 6th ACM International conference on Web Search and Data Mining (WSDM'13), Feb. 4, 2013, pp. 264-274, ACM, United States.

* cited by examiner

TRIGGERING GEOLOCATION FIX ACQUISITIONS ON TRANSITIONS BETWEEN PHYSICAL STATES

CROSS-REFERENCE TO RELATED APPLICATIONS

This application claims the priority benefit of U.S. Provisional Patent Application Ser. No. 61/846,463, filed Jul. 15, 2013, incorporated herein by reference in its entirety.

TECHNICAL FIELD

One or more embodiments generally relate to triggering geolocation fix acquisition, in particular, to acquiring geolocation fix information based on a transition between sensed activity.

BACKGROUND

Location-based applications (LBAs) running on smartphones offer features that leverage the user's current or past physical geolocation (e.g., represented as latitude, longitude coordinates) to provide some enhanced service. While such capabilities are compelling, they are limited in practice due to the high rate of energy consumption from the geolocation fix acquisition process, either through global positioning system (GPS) or trilateration using Wi-Fi or cellular towers.

Continuous use of a GPS sensor can deplete a smartphone's battery within a short time period (e.g., one day). Further, if the periodicity of the fixes has a long inter-acquisition time or if it is irregularly scheduled to reduce power consumption, then successive acquisitions may miss an important geolocation event.

SUMMARY

One or more embodiments generally relate to triggering acquisition of geolocation fix information. In one embodiment, a method provides determining activity state information based on information from one or more sensors. It is determined if an activity state has transitioned to a particular activity state based on the activity state information. Geolocation fix information is acquired if the activity state transitioned to the particular activity state.

In one embodiment, an electronic device comprises one or more sensors that provide sensed data. An activity recognizer determines activity state information based on the sensed data. A transition manager determines if an activity state has transitioned to a particular activity state based on the activity state information. A geolocation service or geolocation sensor acquires geolocation fix information if the activity state transitioned to the particular activity state.

In one embodiment a non-transitory computer-readable medium having instructions which when executed on a computer perform a method comprising: determining activity state information based on sensed data. It is determined if an activity state has transitioned to a particular activity state based on the activity state information. Geolocation fix information is acquired if the activity state transitioned to the particular activity state.

These and other aspects and advantages of one or more embodiments will become apparent from the following detailed description, which, when taken in conjunction with the drawings, illustrate by way of example the principles of the one or more embodiments.

BRIEF DESCRIPTION OF THE DRAWINGS

For a fuller understanding of the nature and advantages of the embodiments, as well as a preferred mode of use, reference should be made to the following detailed description read in conjunction with the accompanying drawings, in which.

DETAILED DESCRIPTION

Figure 1:
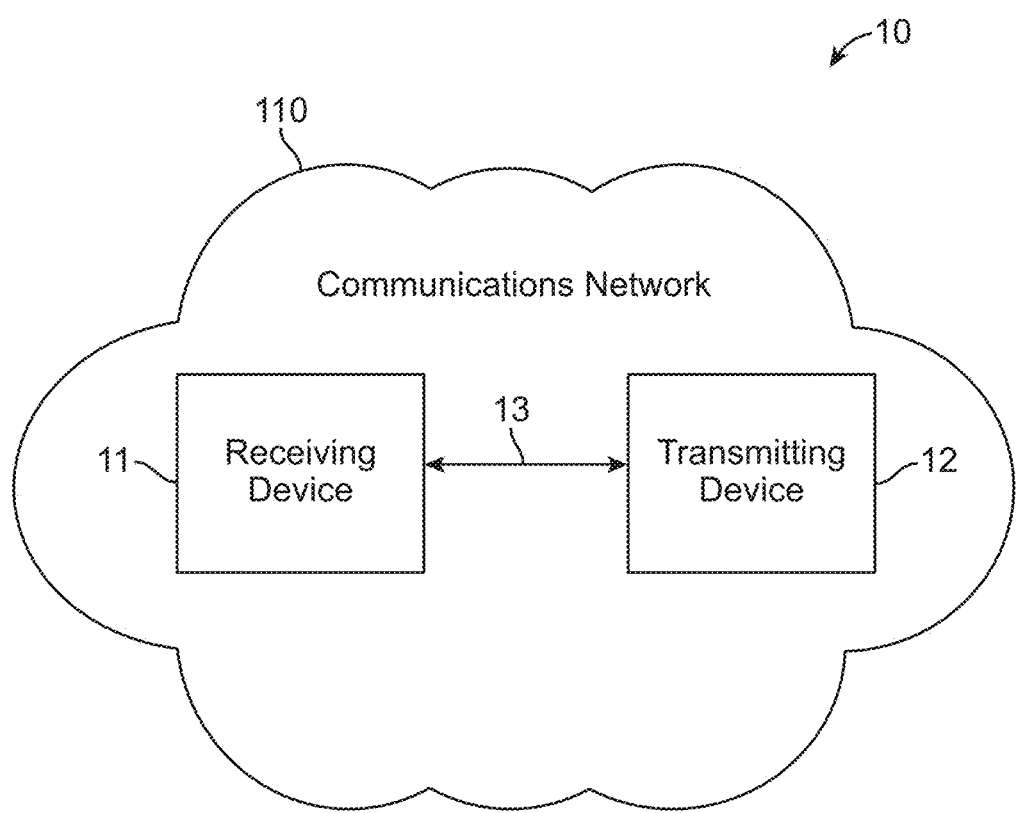
FIG. 1 shows a schematic view of a communications system, according to an embodiment.

The following description is made for the purpose of illustrating the general principles of one or more embodiments and is not meant to limit the inventive concepts claimed herein. Further, particular features described herein can be used in combination with other described features in each of the various possible combinations and permutations. Unless otherwise specifically defined herein, all terms are to be given their broadest possible interpretation including meanings implied from the specification as well as meanings understood by those skilled in the art and/or as defined in dictionaries, treatises, etc.

Embodiments relate to triggering geolocation fix acquisition (e.g., longitude and latitude coordinates, longitude, latitude, altitude coordinates, etc.) based on activity transitioning determined from sensed data. In one embodiment, a method includes determining activity state information based on information from one or more sensors. It is determined if an activity state has transitioned to a particular activity state based on the activity state information. Geolocation fix information is acquired if the activity state transitioned to the particular activity state.

One or more embodiments invoke geolocation acquisition at the transitions between user physical activities, such as between periods of driving and walking or between periods of long idling and bicycling. These transition points typically mark a location where the user has arrived or departed and is amenable to engagement with a location based application (LBA), and a geolocation fix is triggered on these transitions. In one example, if a user has been driving and then transitions to walking, then most likely the user has parked his car and gotten out to walk, and that moment would be an opportunity to acquire a geolocation fix to see if it satisfies any LBA. In other examples, other identifiable transitions are also good opportunities for acquiring a geolocation fix.

In one example, a user's physical activity, such as walking, running, traveling (e.g., airplane, train, boat, bicycle, tram, etc.) or driving, can be accurately determined through a low-power, high-resolution activity recognition system that uses only a smartphone accelerometer and classification processing, which may be measured to consume, for example, 30 mW (on top of an active CPU, which consumes about 180 mW). In one embodiment, no continuous GPS tracking is performed, and GPS tracking is not enabled whenever the user is in motion.

One or more embodiments make a low-power determination to acquire a geolocation coordinate only at when it is needed, namely at transitions between major human activities. In one example, just an accelerometer sensor and classification using the sensed data is performed, which consumes much less power than continuous GPS or cell radio polling. In one embodiment, the activity recognition differentiates between fine-grained activities, such as sitting and driving, and as a result makes distinctions between activities accurately. In one embodiment, if the geolocation acquisition is triggered only upon transitions, it may not be triggered if the user is continuously performing the same activity, such as constantly driving or walking. In one embodiment, geolocation acquisition may be periodically performed based on a continuous activity, e.g. every 15 minutes, every 30 minutes, etc.

FIG. 1 is a schematic view of a communications system 10, in accordance with one embodiment. Communications system 10 may include a communications device that initiates an outgoing communications operation (transmitting device 12) and a communications network 110, which transmitting device 12 may use to initiate and conduct communications operations with other communications devices within communications network 110. For example, communications system 10 may include a communication device that receives the communications operation from the transmitting device 12 (receiving device 11). Although communications system 10 may include multiple transmitting devices 12 and receiving devices 11, only one of each is shown in FIG. 1 to simplify the drawing.

Any suitable circuitry, device, system or combination of these (e.g., a wireless communications infrastructure including communications towers and telecommunications servers) operative to create a communications network may be used to create communications network 110. Communications network 110 may be capable of providing communications using any suitable communications protocol. In some embodiments, communications network 110 may support, for example, traditional telephone lines, cable television, Wi-Fi (e.g., an IEEE 802.11 protocol), Bluetooth®, high frequency systems (e.g., 900 MHz, 2.4 GHz, and 5.6 GHz communication systems), infrared, other relatively localized wireless communication protocol, or any combination thereof. In some embodiments, the communications network 110 may support protocols used by wireless and cellular phones and personal email devices. Such protocols may include, for example, GSM, GSM plus EDGE, CDMA, quadband, and other cellular protocols. In another example, a long range communications protocol can include Wi-Fi and protocols for placing or receiving calls using VOIP, LAN, WAN, or other TCP-IP based communication protocols. The transmitting device 12 and receiving device 11, when located within communications network 110, may communicate over a bidirectional communication path such as path 13, or over two unidirectional communication paths. Both the transmitting device 12 and receiving device 11 may be capable of initiating a communications operation and receiving an initiated communications operation.

The transmitting device 12 and receiving device 11 may include any suitable device for sending and receiving communications operations. For example, the transmitting device 12 and receiving device 11 may include mobile telephone devices, television systems, cameras, camcorders, a device with audio video capabilities, tablets, wearable devices, and any other device capable of communicating wirelessly (with or without the aid of a wireless-enabling accessory system) or via wired pathways (e.g., using traditional telephone wires). The communications operations may include any suitable form of communications, including for example, voice communications (e.g., telephone calls), data communications (e.g., e-mails, text messages, media messages), video communication, or combinations of these (e.g., video conferences).

Figure 2:
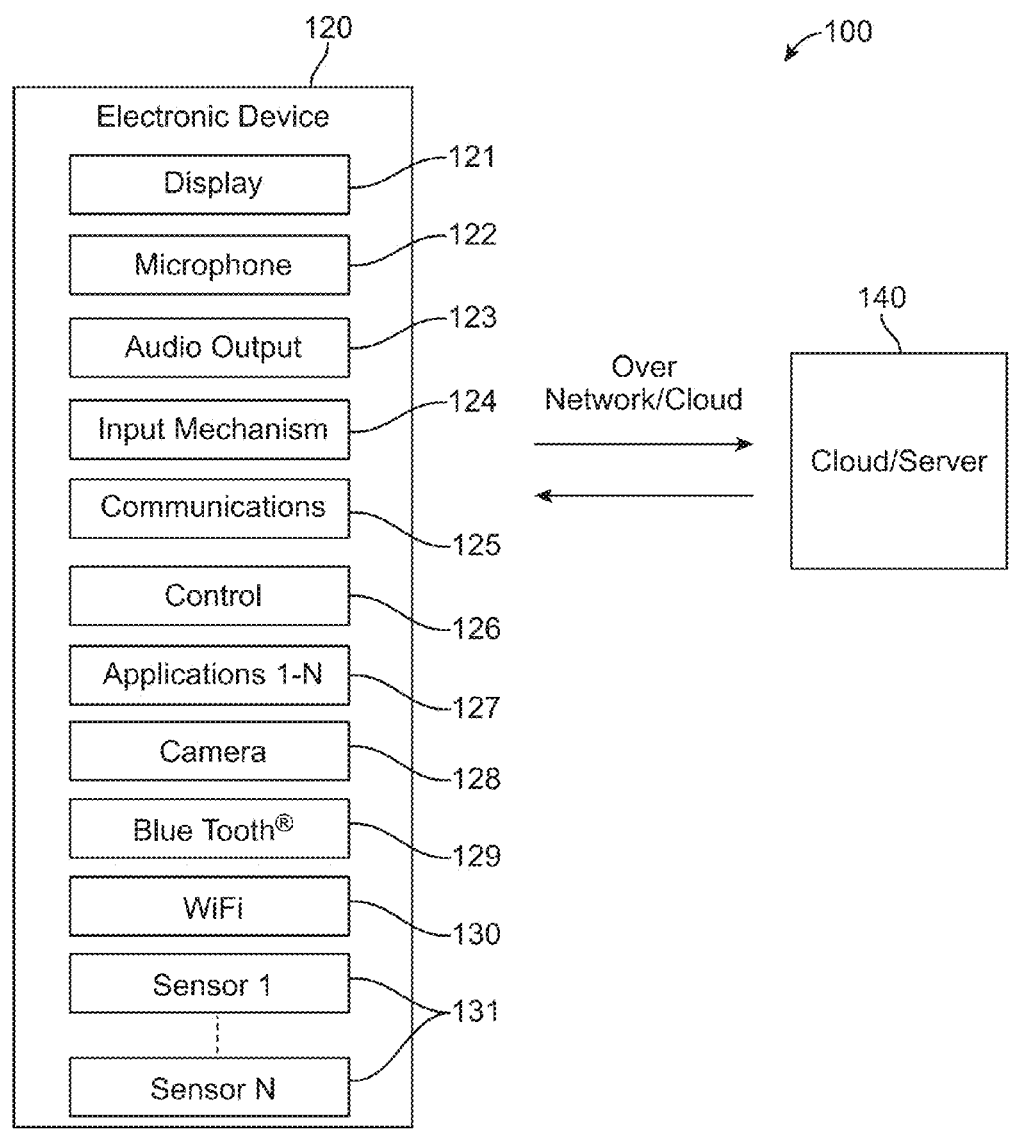
FIG. 2 shows a block diagram of architecture for a system including a server and one or more electronic devices, according to an embodiment.

FIG. 2 shows a functional block diagram of an architecture system 100 that may be used for triggering geolocation fix acquisition based on activity transitioning using an electronic device 120. Both the transmitting device 12 and receiving device 11 may include some or all of the features of the electronics device. In one embodiment, the electronic device 120 may communicate with one another, synchronize data, information, content, etc. with one another and provide complimentary or similar features.

In one embodiment, the electronic device 120 may comprise a display 121, a microphone 122, an audio output 123, an input mechanism 124, communications circuitry 125, control circuitry 126, Applications 1-N 127, a camera module 128, a BlueTooth® module 129, a Wi-Fi module 130 and sensors 1 to N 131 (N being a positive integer), and any other suitable components. In one embodiment, applications 1-N 127 are provided and may be obtained from a cloud or server 140, a communications network 110, etc., where N is a positive integer equal to or greater than 1. In one embodiment, the system 100 includes an activity a geolocation triggering application that may work in combination with a cloud-based server or server 140 to assist in training for activity recognition, by itself, or a combination of the two. In one embodiment, a wearable device may include a portion or all of the features, components and modules of electronic device 120.

In one embodiment, all of the applications employed by the audio output 123, the display 121, input mechanism 124, communications circuitry 125, and the microphone 122 may be interconnected and managed by control circuitry 126. In one example, a handheld music player capable of transmitting music to other tuning devices may be incorporated into the electronics device 120.

In one embodiment, the audio output 123 may include any suitable audio component for providing audio to the user of electronics device 120. For example, audio output 123 may include one or more speakers (e.g., mono or stereo speakers) built into the electronics device 120. In some embodiments, the audio output 123 may include an audio component that is remotely coupled to the electronics device 120. For example, the audio output 123 may include a headset, headphones, or earbuds that may be coupled to communications device with a wire (e.g., coupled to electronics device 120 with a jack) or wirelessly (e.g., Bluetooth® headphones or a Bluetooth® headset).

In one embodiment, the display 121 may include any suitable screen or projection system for providing a display visible to the user. For example, display 121 may include a screen (e.g., an LCD screen) that is incorporated in the electronics device 120. As another example, display 121 may include a movable display or a projecting system for providing a display of content on a surface remote from electronics device 120 (e.g., a video projector). Display 121 may be operative to display content (e.g., information regarding communications operations or information regarding available media selections) under the direction of control circuitry 126.

In one embodiment, input mechanism 124 may be any suitable mechanism or user interface for providing user inputs or instructions to electronics device 120. Input mechanism 124 may take a variety of forms, such as a button, keypad, dial, a click wheel, or a touch screen. The input mechanism 124 may include a multi-touch screen.

In one embodiment, communications circuitry 125 may be any suitable communications circuitry operative to connect to a communications network (e.g., communications network 110, FIG. 1) and to transmit communications operations and media from the electronics device 120 to other devices within the communications network. Communications circuitry 125 may be operative to interface with the communications network using any suitable communications protocol such as, for example, Wi-Fi (e.g., an IEEE 802.11 protocol), Bluetooth®, high frequency systems (e.g., 900 MHz, 2.4 GHz, and 5.6 GHz communication systems), infrared, GSM, GSM plus EDGE, CDMA, quadband, and other cellular protocols, VOIP, TCP-IP, or any other suitable protocol.

In some embodiments, communications circuitry 125 may be operative to create a communications network using any suitable communications protocol. For example, communications circuitry 125 may create a short-range communications network using a short-range communications protocol to connect to other communications devices. For example, communications circuitry 125 may be operative to create a local communications network using the Bluetooth® protocol to couple the electronics device 120 with a Bluetooth® headset.

In one embodiment, control circuitry 126 may be operative to control the operations and performance of the electronics device 120. Control circuitry 126 may include, for example, a processor, a bus (e.g., for sending instructions to the other components of the electronics device 120), memory, storage, or any other suitable component for controlling the operations of the electronics device 120. In some embodiments, a processor may drive the display and process inputs received from the user interface. The memory and storage may include, for example, cache, Flash memory, ROM, and/or RAM/DRAM. In some embodiments, memory may be specifically dedicated to storing firmware (e.g., for device applications such as an operating system, user interface functions, and processor functions). In some embodiments, memory may be operative to store information related to other devices with which the electronics device 120 performs communications operations (e.g., saving contact information related to communications operations or storing information related to different media types and media items selected by the user).

In one embodiment, the control circuitry 126 may be operative to perform the operations of one or more applications implemented on the electronics device 120. Any suitable number or type of applications may be implemented. Although the following discussion will enumerate different applications, it will be understood that some or all of the applications may be combined into one or more applications. For example, the electronics device 120 may include an automatic speech recognition (ASR) application, a dialog application, a map application, a media application (e.g., QuickTime, MobileMusic.app, or MobileVideo.app, Youtube®, etc.), social networking applications (e.g., Facebook®, Twitter®, etc.), an Internet browsing application, etc. In some embodiments, the electronics device 120 may include one or multiple applications operative to perform communications operations. For example, the electronics device 120 may include a messaging application, a mail application, a voicemail application, an instant messaging application (e.g., for chatting), a videoconferencing application, a fax application, or any other suitable application for performing any suitable communications operation.

In some embodiments, the electronics device 120 may include a microphone 122. For example, electronics device 120 may include microphone 122 to allow the user to transmit audio (e.g., voice audio) for speech control and navigation of applications 1-N 127, during a communications operation or as a means of establishing a communications operation or as an alternative to using a physical user interface. The microphone 122 may be incorporated in the electronics device 120, or may be remotely coupled to the electronics device 120. For example, the microphone 122 may be incorporated in wired headphones, the microphone 122 may be incorporated in a wireless headset, the microphone 122 may be incorporated in a remote control device, etc.

In one embodiment, the camera module 128 comprises one or more camera devices that include functionality for capturing still and video images, editing functionality, communication interoperability for sending, sharing, etc. photos/videos, etc.

In one embodiment, the BlueTooth® module 129 comprises processes and/or programs for processing BlueTooth® information, and may include a receiver, transmitter, transceiver, etc.

In one embodiment, the electronics device 120 may include multiple sensors 1 to N 131, such as accelerometer, gyroscope, microphone, temperature, light, barometer, magnetometer, compass, radio frequency (RF) identification sensor, GPS, etc. In one embodiment, the multiple sensors 1-N 131 provide information to a geolocation triggering application 127.

In one embodiment, the electronics device 120 may include any other component suitable for performing a communications operation. For example, the electronics device 120 may include a power supply, ports, or interfaces for coupling to a host device, a secondary input mechanism (e.g., an ON/OFF switch), or any other suitable component.

Figure 3:
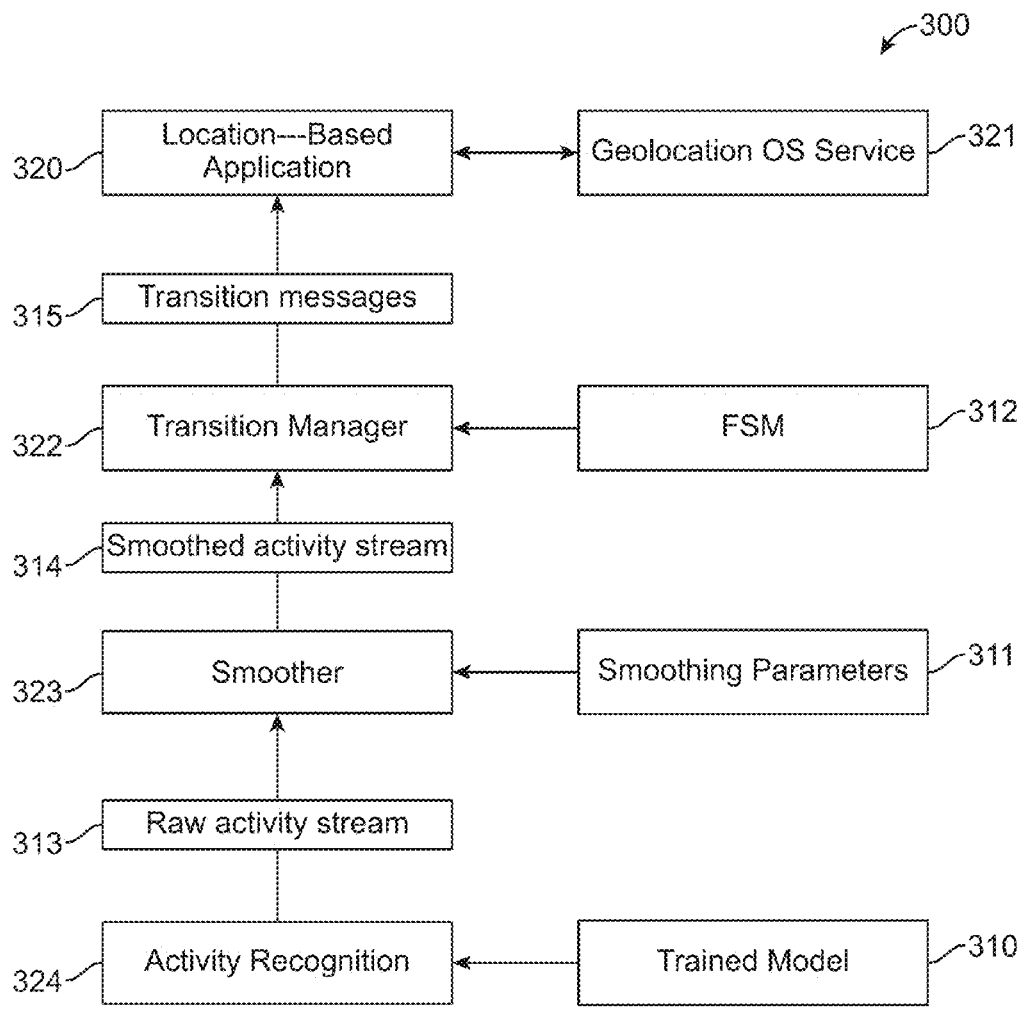
FIG. 3 shows a high-level architecture for a system, according to an embodiment.

FIG. 3 shows a high-level architecture for a system 300, according to an embodiment. While there exist many location-based application (LBA) domains that require continuous geolocation tracking, such as health monitoring and vehicular traffic aggregation, one or more embodiments may be used with LBAs for which continuous tracking is superfluous and unnecessarily depletes the battery of an electronic device (e.g., electronic device 120, FIG. 2). These LBAs may need a geolocation fix only at rare points during the day. Automatically and intelligently triggering geolocation acquisition just as it is needed for these types of applications produces the tangible benefit of increased battery life for users. For example, consider a user that wants to set a location-based reminder. While the user is at work, he/she creates an alert that should activate when he/she arrives at his targeted home. Assume that the home's address is in his/her smartphone's address book and has already been resolved to a geocoordinate. Such a reminder can be implemented in a number of ways. For continuous tracking, the system can continuously track the user as he/she drives from work to home. To save power, it can use coarse-grained but lower-power cellular tower geopositioning to determine the user's location with an error of about 300 m to 400 m. When the user is within that error range to his/her home, the system may switch to GPS to get accuracy to within 10 m. Once the user is within a proximity tolerance of the target, the reminder system activates the alert.

In one embodiment, the system 300 provides a just-in-time geolocation fix. The system 300 may trigger one geolocation fix just as the user arrives at his/her home, and because he/she is within a proximity tolerance, the reminder system activates the alert. For sensor fingerprinting to derive semantic location, the system can use sensor fingerprints (i.e. features extracted from on-device sensors) to infer that the user has arrived at his home, which is a semantic location rather than a geocoordinate. For example, Wi-Fi, Bluetooth®, audio, light, and other sensors as inputs to a classifier may be used. Since this approach requires training fingerprints to be taken, its generalizability is still an open question.

In one embodiment, while triggering a geolocation fix acquisition before knowing that the user has arrived at a location may seem oracular, triggering may be implemented in a general manner by observing transitions between user activity states, where each state represents a mode of transportation. In one example, particular transitions are indicative of moments in time when the user is amenable to engagement with an LBA, and so a fix is triggered on these transitions.

In one embodiment, the system 300 the following data or models comprise a physical activity trained model 310, smoothing parameters 311, a finite state machine (FSM) model 312, a raw activity stream 313, a smoothed activity stream 314 and transition messages 315. In one embodiment, the system 300 includes the following modules or applications: a location based processing module or application 320, a geolocation operating system (OS) service 321 (e.g., GPS information, triangulation information, Wi-Fi information, etc.), a transition manager 322, a smoother 323 and an activity recognizer or recognition process or module. In one example, at the bottom-most layer, a low-power accelerometer-only activity recognition component generates a continuous stream of inferred human modes of transportation. This component uses a supervised machine learning classifier that loads a trained (e.g., C4.5) decision tree model into memory, reads real-time accelerometer signals, and produces a classification label. While the activity recognition is accurate on single-activity behavior, it produces endemic misclassification errors when faced with real-world, mixed-activity behavior. To address this problem, a smoothing window is applied by the smoother 323.

The transition manager 322 listens to the stream of smoothed activity labels and manages an FSM to detect relevant transitions. The vertices and edges in the FSM have labels that correspond to the possible activity recognition labels. The output of the transition manager 322 are transition messages 315 sent to any listening application (e.g., LBA 320). In one example, for an Android-specific implementation, these messages are realized as Android Intents.

Upon receiving such a transition message 315, the listening LBA 320 then acquires a geolocation fix from geolocation OS service 321 and checks to see if the resulting geolocation coordinate satisfies its LBA-specific logic. For example, the coordinate may trigger a location-based reminder or a location-based advertisement. In one example, the transition manager 322 acquires the geolocation and then includes the resulting coordinates in its Intent message to all listeners. It should be noted that this example would bypass Android's security and privacy model where each application must declare its use of geolocation services (in its manifest file), which is then surfaced to the user in the application's description before it can be downloaded from an application store.

Figure 4:
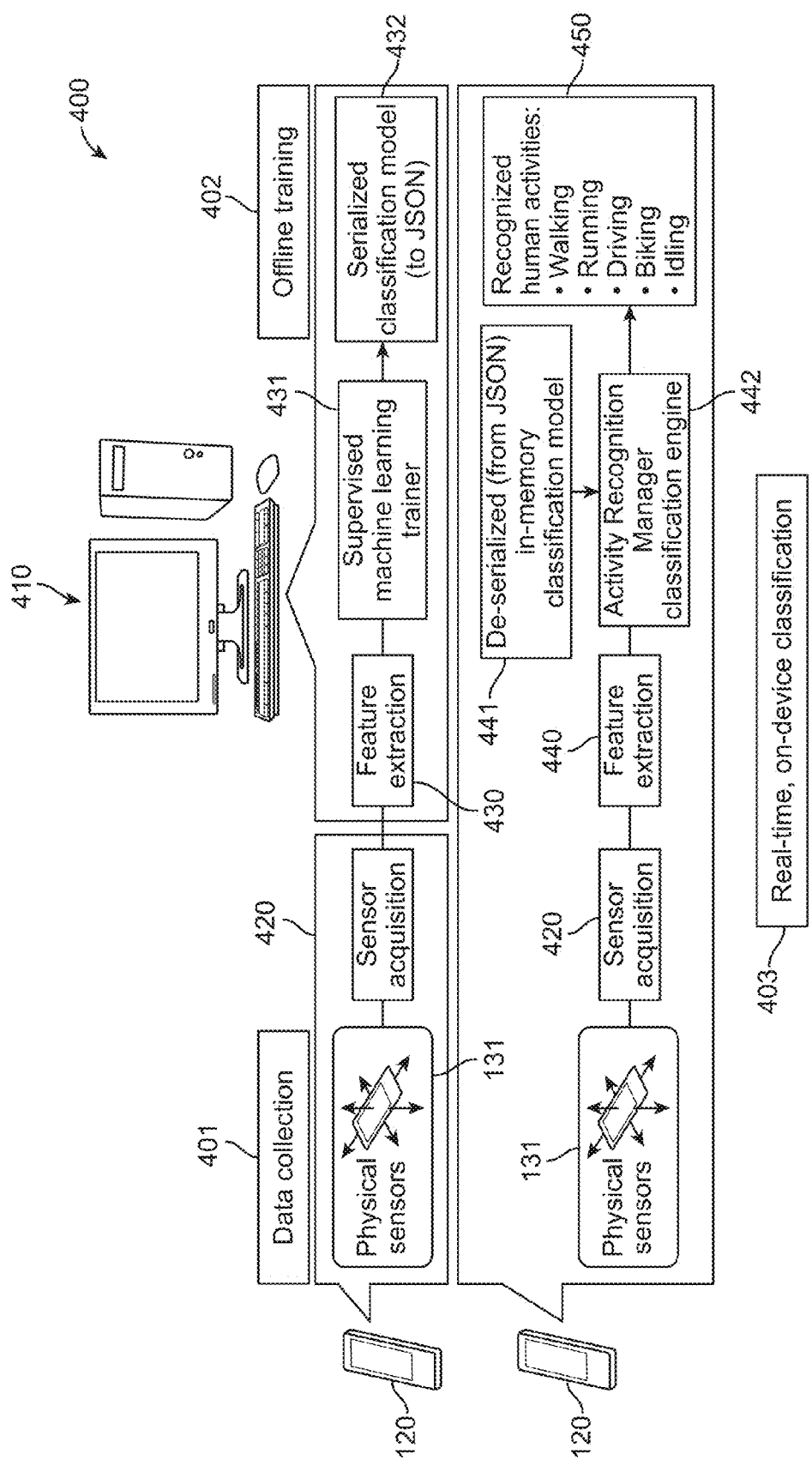
FIG. 4 shows an example activity recognition end-to-end data collection, training and classification flow, according to an embodiment.

FIG. 4 shows an example activity recognition end-to-end data collection, training and classification flow 400, according to an embodiment. Smartphone-based physical activity recognition infers human activities by analyzing on-board smartphone sensor signals, and in one embodiment supervised machine learning at 431 is used to make these inferences. The end-to-end system flow 400 comprises two distinct phases. First, in an offline training phase 402, test participants perform various physical activities using while each wearing or holding an electronic device 120 (e.g., a smartphone) with physical sensors 131 that runs a data-collection application for sensor acquisition 420 (i.e., data collection 401). After extracting relevant sensor features at 430 and 440, the model is then trained that maps such features back to the physical activities using the supervised machine learning trainer 431. Second, in an online classification phase 403 that runs on an electronic device 120 (e.g., a smartphone), the model is deployed onto electronic device's 120 and loaded by the activity recognition manager (classification engine) 442 to perform on-board, real-time classification of sensor data that can drive higher-level applications.

In one example embodiment, the activity recognition manager's 442 sole input is the accelerometer sensed data, and the periodic output is a callback containing an activity represented as a string, such as Running; downstream clients then implement callback listener functions to receive them. In one example, the following recognized activities 450 may be defined: Walking, Running, Driving, Bicycling, and Idling (which comprises standing and sitting). It should be noted that other activities may be defined, such as traveling (e.g., by air (e.g., an airplane, helicopter, etc.), sea/water (e.g., boat, ship, etc.), land (e.g., bicycling, train, trolley, etc.), etc.).

In one example, to train the supervised machine learning model 431, users perform single-activity, scripted behavior while an application (e.g., running on an electronic device 120) recorded tri-axis accelerometer readings at a particular frequency (e.g., 32 Hz) and labelled them with the user's activity. In each resulting file, for example, the first ten and the last ten seconds' worth of samples are trimmed off. In one example, for seventeen (17) total users, (e.g., men/women in their twenties to fifties), data totaled 397 minutes, or over 6 hours, across the activities mentioned earlier: walking (on a flat surface), walking up stairs, walking down stairs, running, bicycling, driving, standing, and sitting. The users were requested to hold smartphones in any way they wanted, but most ended up placing the phone in their front right pants pocket. For sitting, users placed the phone either in that pocket or on a desk surface. For driving, users placed the smartphone either in their pocket, in a bag, or on a windshield-attached cradle. For bicycling, users placed the smartphone in a belt-mounted hip holster.

Because a smartphone can be oriented in different directions on a person's body, in one example the accelerometer readings are normalized into three orientation-independent time series: Cartesian magnitude of the acceleration vector; magnitude of projection onto the true horizontal plane; and projection onto the true vertical axis. To derive the latter two time series, one embodiment computes the dynamic component of device acceleration in the true global vertical plane and the true horizontal plane perpendicular to the vertical plane. The resulting three time series (Cartesian magnitude of the acceleration vectors, magnitude of projection onto the true horizontal plane, and projection onto the true vertical axis) are then captured with a 128-sample sliding window with 50% overlap. For each of the three time series, features are computed using both the time and frequency domains. To obtain frequency domain information, a fast Fourier transform (FFT) is ran and standard steps are performed to compute a correctly-scaled magnitude frequency response. In one example, the features used are:

- time-domain mean,
- time-domain standard deviation,
- time-domain real-valued discrete power,
- time-domain entropy,
- frequency-domain energy,
- the frequency fmax with the highest magnitude,
- the magnitude of fmax,
- the frequency fweighted-mean calculated as the weighted mean of the top-5 highest-magnitude frequencies weighted by magnitude, and
- the weighted variance of the top-5 highest-magnitude frequencies weighted by magnitude.

The above nine features are extracted at 430 from each of the three time series, resulting in 27 total features that are concatenated together into one feature vector. In one example, off-the-shelf machine learning programs may be used to build the offline model 402 on a desktop computer. The software provides a variety of different machine algorithms, including Naive Bayes, SVM, and kNN, and after testing, it was found that the C4.5 multi-class decision tree produced the best results. Additional benefits of using a decision tree are that its memory footprint is low (less than 10 kB resident in memory) and its time to classify a feature vector is small (on the order of milliseconds), characteristics that are important when executing on a device such as a smartphone. Classifying a real-valued feature vector is a matter of walking down a tree structure and making a single floating-point comparison at each level. The resulting trained model is serialized at 432 to a JSON file that contains data structures, statistics, and other metadata that are deserialized at 441 later on the electronic device 120 by the activity recognition manager 442. The serialization format is JSON rather than binary, resulting in a file that is portable and may be deployed and updated separately from the other activity recognition components.

The on-device classification phase 403 of system 400 comprises several stages and a trained model. In one embodiment, the sensor acquisition layer 420 is the interface between the classification system and the sensor API provided by the electronic device's 120 operating system. The sensor acquisition layer 420 is responsible for (i) reading the physical hardware sensors 131 (FIG. 2), such as an accelerometer (or other sensors, such as a microphone 122 and compass), and (ii) preparing the data into a structure for later processing. The activity recognition manager 442 runs as a system-wide singleton service 441 that (i) loads the JSON-encoded classification model built during the offline training phase 402, (ii) reads accelerometer input from the sensor acquisition layer 420 to extract features at 440, and (iii) executes the real-time activity classification. In one example, clients register themselves as listeners to the activity recognition manager 442, which then invokes client callback functions whenever a relevant activity has been recognized by the classifier of the activity recognition manager 442.

In one embodiment, the classifier of the activity recognition manager 442 is augmented with a smoother 323 (FIG. 3) for providing a smoothing algorithm that improves classification for real-world usage. In one example, the system 400 achieves a ten-fold cross-validated accuracy of 98.4%. To avoid any such choppiness, in one example a simple smoothing algorithm is employed with a majority vote within a trailing window (of parameter size N). As described below, this choice of N affects the trade-off between the number of geolocation fix requests and the delay (in terms of time and distance) between the geolocation fix request and ground-truth observed transitions.

Figure 5:
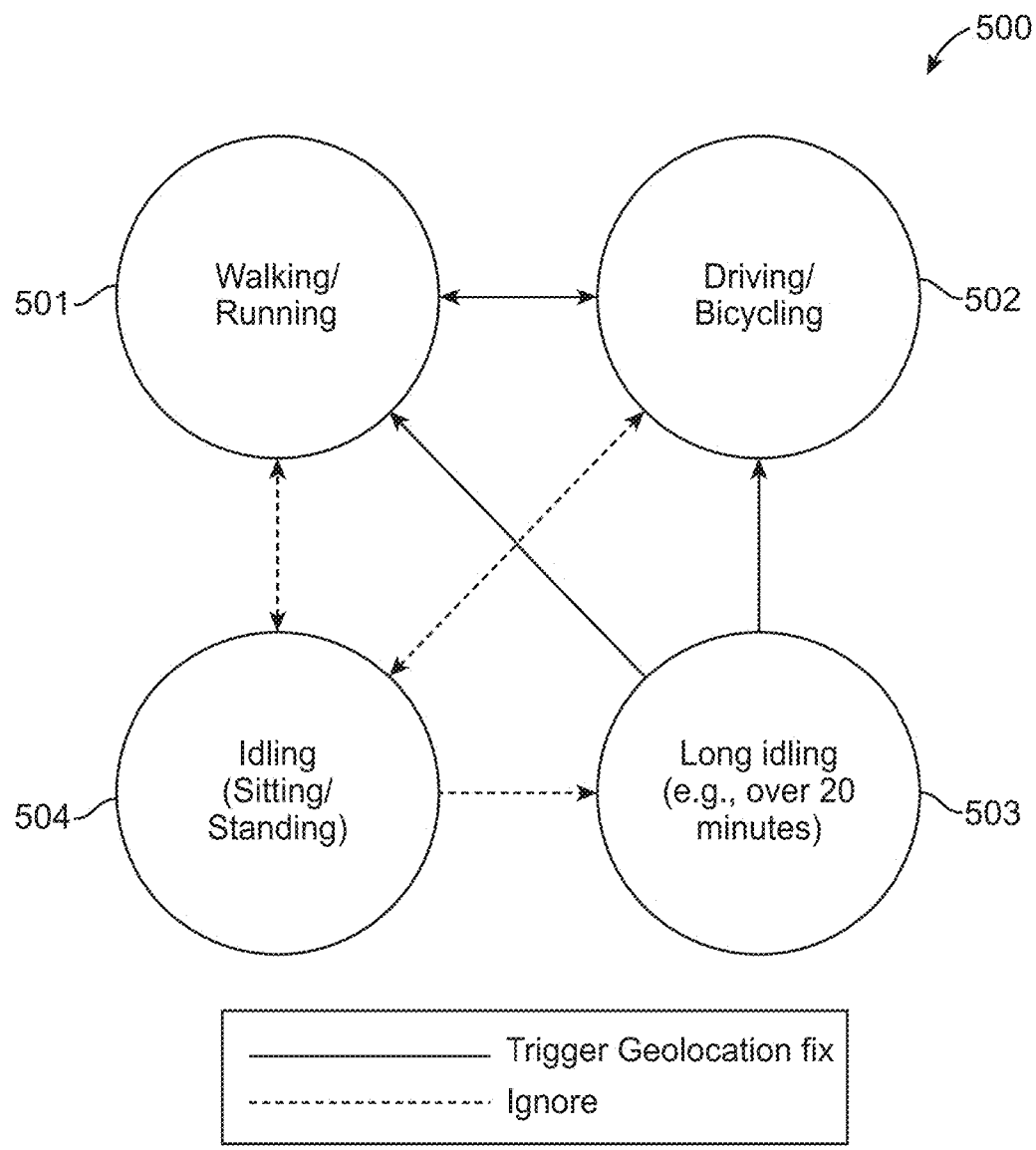
FIG. 5 shows an example of geolocation fixes triggered based on activity transitions controlled by a finite state machine (FSM), according to an embodiment.

FIG. 5 shows an example 500 of geolocation fixes triggered based on activity transitions controlled by an FSM, according to an embodiment. Given the availability of the low-power activity recognition system 300/400 (FIG. 3, FIG. 4) described above, its output states (comprising recognized modes of transportation) are used as input into our just-in-time geolocation fix component. In one embodiment, certain transitions or transition pairs between modes of transportation are indicative of points in time that are more conducive to user engagement with LBAs. For example, when the user makes the transition Driving 502→Walking 501, it may indicate that they have gotten out of their car after having arrived at a desired destination. This spot would then be a good opportunity for an LBA to acquire a geolocation fix to see if it satisfies its LBA-specific logic. Note that in the case of a location-based reminder with the user's home as the target destination, this approach will still trigger a geolocation acquisition if the user stops somewhere else first, such as at a gas station. Nonetheless, as described below these additional acquisitions are still less frequent than continuous geolocation tracking.

In one example, the transition manager 322 (FIG. 3) observes the smoothed activity recognition stream and keeps track of the current and immediately previous user state. By observing these two states, the transition manager 322 may identify transitions between certain activities, where these transitions are represented as edges within an FSM. The reference FSM is shown as the example 500. Note that most of the vertices in the example 500 correspond to the available known activity labels that may be produced by the activity recognizer 324. In one example, the only special vertex is the one for long idling 503, which is defined to be idling (e.g., sitting or standing) for more than a particular fixed period of time (e.g., twenty minutes, thirty minutes, etc.).

When a transition between states is detected by the transition manager 322, the FSM is checked to determine if the transition qualifies for a geolocation fix acquisition. In one example, the solid edges in the FSM example 500 are those transitions that are selected to trigger an acquisition. These transitions were heuristically selected to be those where an LBA would most likely take advantage of a new geolocation. In one example, transitions from idling 504 (e.g., siting/standing) to walking/running 501, driving/bicycling 502 and long idling 503 does not trigger a geolocation fix acquisition.

Different FSMs defining different transitions may be used in place of the example 500. In one embodiment, appropriate transitions may be discovered automatically rather than heuristically; building a Hidden Markov Model is one such approach. Unlike conventional systems where accelerometers are used to differentiate between only binary states (e.g., idling vs. non-idling), one or more embodiments leverage the distinction between multiple classes of non-idling, such as between driving 502 and running 501. Note further that being able to be detect these distinctions using only the accelerometer provides a battery consumption advantage over other approaches that use GPS as a sensor. If the user does not change their mode of transportation, then the transition manager 322 is unable to detect any transitions at all. For example, it may be the case that the user continuously walks from their home to work, never stopping at any point. To address this problem, in one example embodiment a background service is implemented that performs fixed duty-cycling with a parameterized period to serve as a backup (e.g., a particular time period, such as 20 minutes as long idling 503).

Figure 6:
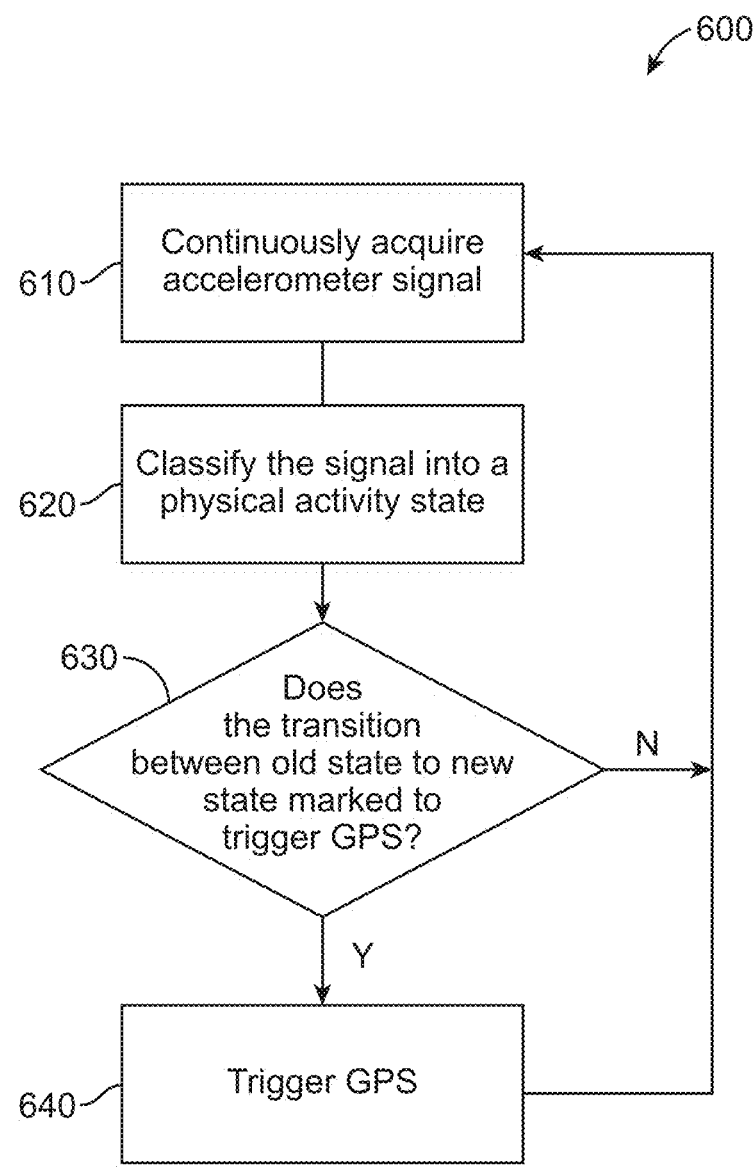
FIG. 6 shows an example flow diagram for triggering geolocation information, according to an embodiment.

FIG. 6 shows an example flow diagram 600 for triggering geolocation information acquisition, according to an embodiment. In one embodiment, block 610 continuously acquires accelerometer signals or sensed data. In block 620, the signal or sensed accelerometer data is classified into a physical activity state or mode. In one embodiment, in block 630 it is determined if a transition between an old state or mode and a new state or mode is marked to trigger a geolocation fix acquisition (e.g., GPS trigger). If it was determined to not mark a transition to trigger a geolocation fix acquisition, the process returns to block 610. If it is determined that a transition triggers a geolocation fix acquisition, in block 640 the acquisition is triggered. In one example, a GPS acquisition is triggered rarely only on specific transitions between modes of transportation, for example, Driving→Walking. In one example, activity recognition is the process of deriving the user's (physical) activity from sensor data (e.g., walking, running, driving, biking, idling, etc.).

Figure 7:
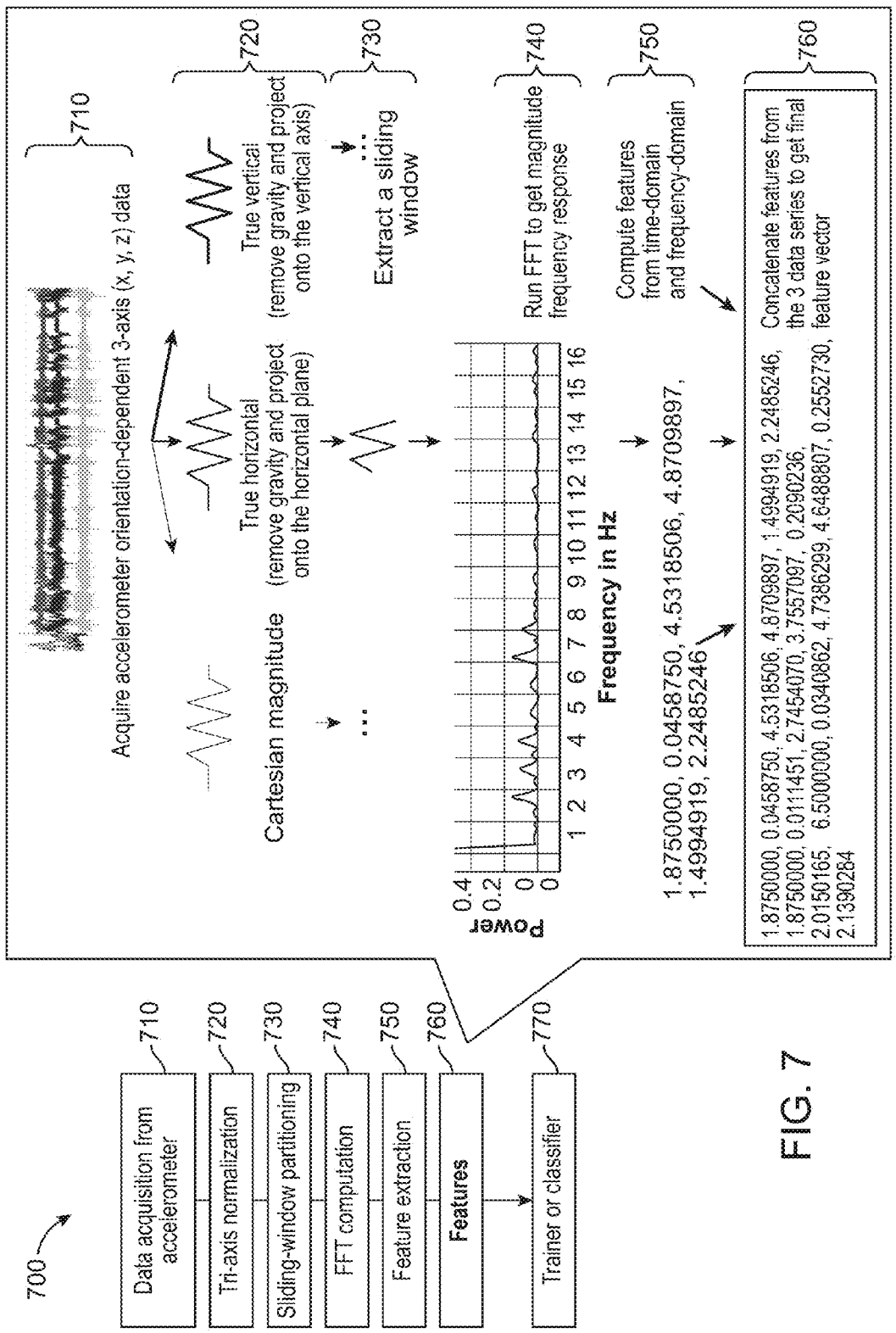
FIG. 7 shows a process flow for determining activity state changes, according to an embodiment.

FIG. 7 shows a process flow 700 for determining activity state changes, according to an embodiment. In one embodiment, the flow 700 includes data acquisition from accelerometer data 710, tri-axis normalization 720, sliding-window partitioning 730, FFT computation 740, feature extraction 750 resulting in features 760 and trainer or classifier 770. In one example implementation, the system for process flow 700 comprised testing on two commodity Android smartphones, a Samsung Galaxy S II (released in the U.S. in May 2011) and a Samsung Nexus S (released in the U.S. in December 2010). The key result from the example implementations is that while the activity recognition transition-triggered design incurs more delay to identify ground-truth events versus competing schemes, it requires significantly fewer geolocation fix acquisitions, (e.g., up to 41× fewer acquisitions) than an accelerometer-assisted binary classification scheme and 243× fewer than continuous tracking over the collected data.

In one example, the raw user activity stream 313 (FIG. 3) that is generated indicates the user's mode of transportation. Using training data set collected from several users (e.g., seventeen users), the system demonstrates a 98.4% per-window classification accuracy over activities with 10-fold cross-validation. The confusion matrix is shown in Table 1. In one example, it was determined that walking up and down stairs is confused often with walking on a flat surface; therefore these activities are aggregated together into a final classifier. Similarly, standing and sitting are aggregated into idling. The end result is an output of five activities: Walking, Running, Driving, Biking, and Idling as shown in the example FSM 500 (FIG. 5). For the example implementation, data was collected from seventeen users (20s to 50s, 15 men, 2 women). In this example, the Android returned samples at 50 or 100 Hz, and the sampling is downsampled to 32 Hz for consistency across smartphones. Features from time and frequency domain were extracted and 128-sample window with 50% overlap is used. Classifications returned every two seconds with four seconds' worth of data. In this example, a C4.5 decision tree classifier is implemented (fast, simple, low power, low memory footprint).

TABLE 1

|  |  | Predicted | | | | | | | |
| --- | --- | --- | --- | --- | --- | --- | --- | --- | --- |
|  |  | Walking | Sitting | Running | Standin | Driving | StairsDow | StairsU | Biking |
| Actual | Walking | 99.05% | 0.00% | 0.09% | 0.06% | 0.12% | 0.15% | 0.34% | 0.18% |
|  | Sitting | 0.00% | 99.24% | 0.00% | 0.51% | 0.13% | 0.00% | 0.00% | 0.13% |
|  | Running | 0.42% | 0.00% | 99.48% | 0.00% | 0.00% | 0.00% | 0.00% | 0.10% |
|  | Standing | 0.00% | 1.33% | 0.00% | 97.52% | 1.14% | 0.00% | 0.00% | 0.00% |
|  | Driving | 0.16% | 0.06% | 0.00% | 0.13% | 99.00% | 0.00% | 0.00% | 0.65% |
|  | StairsDow | 16.83% | 0.00% | 0.00% | 0.00% | 0.00% | 80.20% | 2.97% | 0.00% |
|  | StairsUp | 29.63% | 0.00% | 0.00% | 0.00% | 0.00% | 7.41% | 62.96% | 0.00% |
|  | Biking | 0.56% | 0.00% | 0.00% | 0.00% | 2.33% | 0.00% | 0.00% | 97.11% |

As shown in table 1, overall the example implementations resulted in a 10-fold cross-validated accuracy of 98.4%. Walking up stairs down was merged into the Walking classification. Sitting and standing classifications were merged into the Idling classification. A smoothing window as implemented in order to reduce spurious misclassifications. The power consumption of the activity recognition system was evaluated using a Monsoon Solutions Power Monitor, a hardware power meter that directly provides electricity through connected leads and measures the resulting power draw. The results from both test devices are shown in Table 2 below. In one example, it was found that the continuous recognition consumes up to approximately 225 mW. Note that the activity recognition's signal processing, feature extraction, and classification consumes very little power, whereas the baseline idle CPU (kept alive with a wake lock to ensure that the system continues to run even if the screen is off) consumes the most. As a point of reference, the power consumption of the Galaxy S II to acquire a GPS fix is 771 mW, including the baseline CPU. Power consumption of the activity recognition system on commodity smartphones, where the phones were run in "airplane mode" with no Wi-Fi and the screen off. Total power on the Galaxy S II is 224.92 mW.

TABLE 2

| Smartphone | Baseline idle CPU with wake lock | Accelerometer sampling to 32 Hz | Feature extraction and classification |
|---|---|---|---|
| Samsung Nexus S | 167.15 mW | 18.03 mW | 4.49 mW |
| Samsung Galaxy S II | 184.34 mW | 35.53 mW | 5.05 mW |

The following description provides an evaluation to quantify the performance of activity recognition transition-triggering against competing schemes. Note that the system runs successfully on the example smartphones and correctly triggers geolocation acquisition fixes on transitions between specific modes of transportation; however, to fully evaluate the system with varying parameters, data traces were recorded and ran offline testing to expedite the implementation. Both the online and offline execution used the same base processing.

In these example implementations the users carried two clock-aligned Android smartphones to collect two streams of data over the course of entire days, including overnight. First, to collect ground truth transitions, users carried a phone running an application that recorded the immediate time and geocoordinate when a button is pressed. The users pressed this button at transition moments between modes of transportation which could be appropriate for an LBA to acquire a geolocation fix. Second, to collect traces of sensor data, users carried another phone which they kept with them in any position they wanted. The application on this smartphone continuously recorded accelerometer data and geolocation data. Note that both the ground truth transitions and sensor data collection could have been performed on the same smartphone. In this data set sensor readings were collected totaling 547,583 minutes (or 6.34 days). During this time, users also collected 124 ground-truth transition events of their choice that they believed represented opportunistic locations where an LBA could provide value. These locations turned out to include the users' home, work-place, shopping malls, gas stations, restaurants, and other places. Geolocation fixes were acquired through either GPS or Wi-Fi/cell tower trilateration. Given the two data streams, the system was evaluated against competing geolocation-triggering schemes along the following dimensions:
1. What is the recall of each scheme—that is, what fraction of ground-truth transitions were correctly recognized?
2. What is the delay between the ground-truth observation and the triggered geolocation fix acquisition in terms of time and distance?
3. How many fix acquisitions are triggered by each scheme.

For the example implementation testing, four processes for triggering a geolocation fix acquisition were used: continuous tracking, continuous tracking with fixed duty cycling, accelerometer-assisted, binary states, and Activity Recognition-Triggered, Window N. For continuous tracking, this approach triggers a geolocation fix as often as possible, where the collected data came directly from the sensor-collection phone as described earlier. To enable this approach, the Android's LocationManager class was used and asked for callbacks from either GPS or network services, where the callbacks are set with a minimum time of 1 millisecond and mini-mum distance of 0.1 meters. It is noted that the callback minimum time is not necessarily honored by the underlying location service.

For continuous tracking with fixed duty cycling, this approach triggers acquisitions with a 15-second inter-acquisition period. For accelerometer-assisted, binary states, the accelerometer is used to detect idling versus non-idling. A 4-second segment of accelerometer data is evaluated, and if the user is idling, then geolocalization is deactivated, whereas if the user is not idling (but moving), then the geolocation fixes are acquired as often as possible (using the same settings as Continuous Tracking).

For activity recognition-triggered, window N, this approach represents an example embodiment, where the activity recognition processes described above are applied on the collected sensor data and a smoothing window of size N (which varies between five and forty) is applied. The system then triggers a geolocation fix acquisition only on the transitions shown in the FSM example 500 (FIG. 5).

In the example testing, the recall of each triggering scheme is performed by quantifying the fraction of the 124 ground-truth transition events that were correctly identified for geolocation triggering. A true-positive identification of a ground-truth event is considered as occurred when the scheme performs triggering within 60 seconds of the ground-truth, where a particular triggering can be associated with only one other ground-truth event. In Table 3 below, the recall of each triggering scheme is provided.

TABLE 3

| Triggering Scheme | Rec |
|---|---|
| Continuous Tracking | 0.8 |
| Continuous Tracking | 0.8 |
| Accelerometer-Assisted, | 1.0 |
| Activity Recognition- | 1.0 |
| Activity Recognition- | 0.9 |
| Activity Recognition- | 0.9 |
| Activity Recognition- | 0.8 |
| Activity Recognition- | 0.7 |

Continuous tracking, with and without fixed duty cycling, performed relatively poorly despite the fact that they supposedly trigger geolocation fixes often. The problem is that while the Android API allows the developer to set the minimum time between the automatic geolocation callbacks, it is only a hint to the underlying system software or device driver, which may instead provide the callbacks as it sees fit (for example, it may aggressively try to reduce power by conserving geolocation fix invocations). Occasionally it was observed that long lapses (on the order of 15 minutes) between consecutive geolocation fixes with continuous tracking occurred regardless of whether the user was moving or not.

The accelerometer-assisted, binary states scheme performs well with 100% recall, which is representative of the fact that transitions between transportation modes are captured by the binary accelerometer classifier.

In one example embodiment, the activity recognition-triggered, window N scheme exhibits 100% recall with a window size of 5, but suffers decreasing recall with increasing N. The recall diminishes because a longer smoothing window causes activity recognition convergence to take longer, resulting in missed ground-truth transitions.

Figure 8:
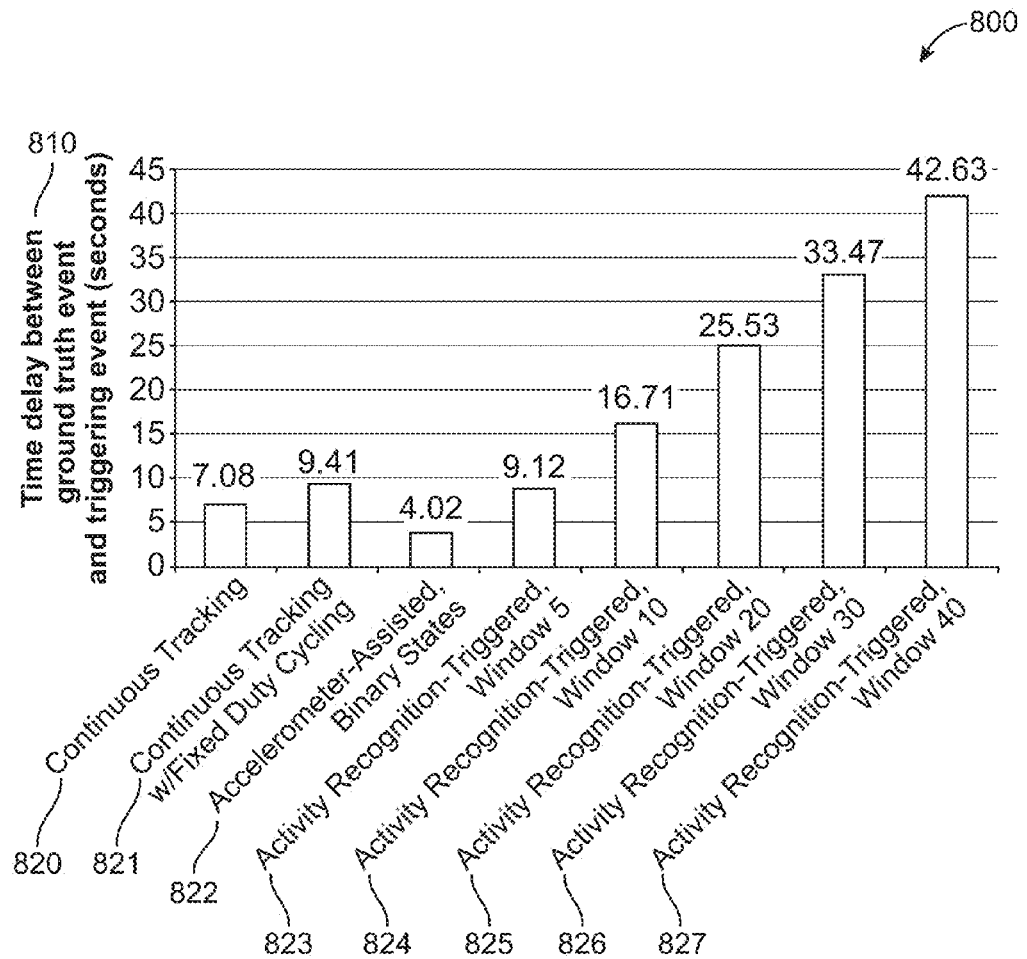
FIG. 8 shows an example comparison for different technologies for time delay between a ground truth event and a triggering event, according to an embodiment.

FIG. 8 shows an example 800 comparison for different technologies for time delay between a ground truth event and a triggering event, according to an embodiment. In the comparison 800, the time delay 810 between the ground truth and triggering events are shown for continuous tracking 820, continuous tracking with fixed duty cycling 821, accelerometer-assisted, binary states 822, and embodiments comprising activity recognition-triggered window 5 823, activity recognition-triggered window 10 824, activity recognition-triggered window 20 825, activity recognition-triggered window 30 826 and activity recognition-triggered window 40 827. Each scheme was evaluated with respect to the delay between the ground-truth transition events and the triggered geolocation acquisition. The median time delay 810 is shown in units of seconds.

It is observed that the continuous tracking 820 scheme has a low time delay, and as expected the continuous tracking with fixed duty cycling 821 set to a 15-second period has a longer delay. The accelerometer-assisted, binary states 822 has the lowest time delay, again illustrating its ability to turn on triggered geolocation fixes as soon as it detects any movement. The activity recognition-triggered, window N scheme (e.g., 823-827) incurs longer delay than, but is competitive against, both continuous tracking 820 and the accelerometer-assisted, binary states 822 scheme with N=5. Note, though, that it again demonstrates decreasing performance with increasing window size. Activity recognition simply responds slower when the smoothing window is large.

Figure 9:
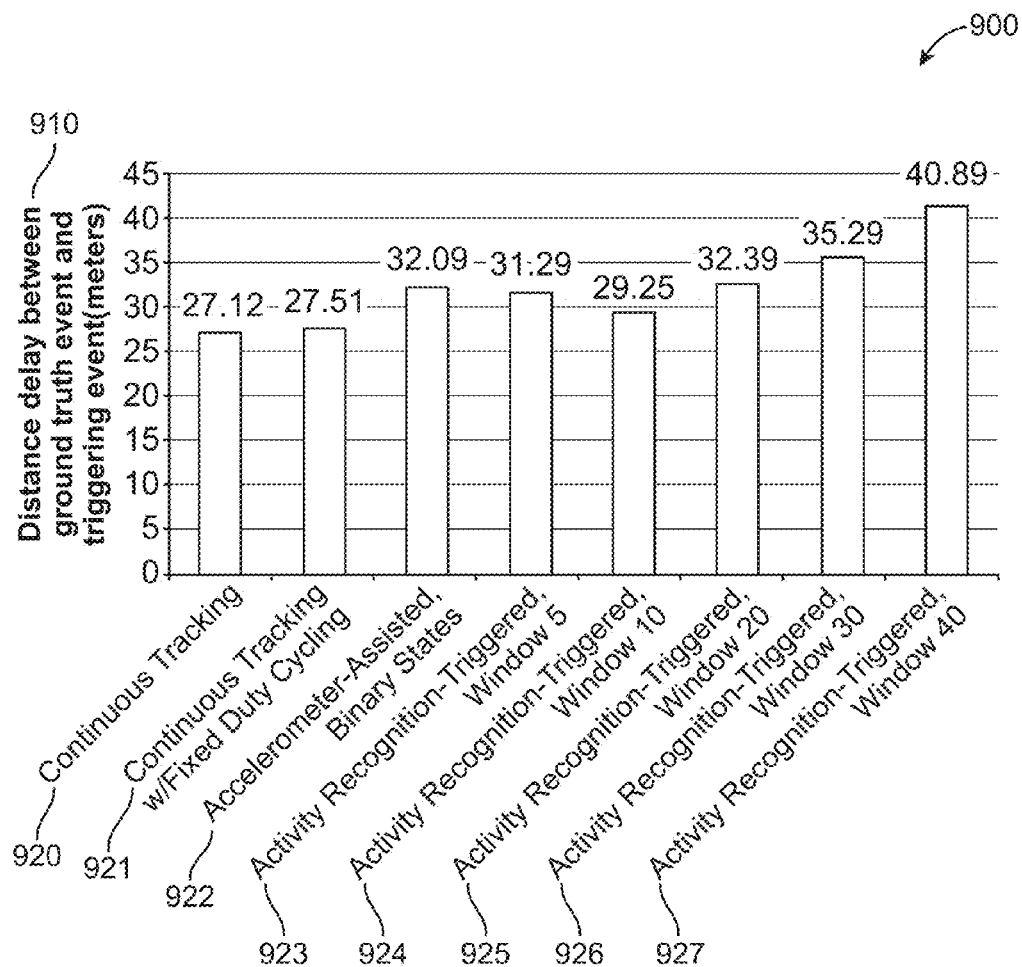
FIG. 9 shows an example comparison for different technologies for distance delay between a ground truth event and a triggering event, according to an embodiment.

FIG. 9 shows an example comparison 900 for different technologies for distance delay 910 between a ground truth event and a triggering event, according to an embodiment. In the comparison 900, the distance delay 910 between the ground truth and triggering events are shown for continuous tracking 920, continuous tracking with fixed duty cycling 921, accelerometer-assisted, binary states 922, and embodiments comprising activity recognition-triggered window 5 923, activity recognition-triggered window 10 924, activity recognition-triggered window 20 925, activity recognition-triggered window 30 926 and activity recognition-triggered window 40 927. The median distance delay is shown in units of meters, where the Haversine distance from the latitude and longitude coordinates is calculated. Note that any distance between the time of the ground-truth event and the time of the triggering is dependent on the mode of transportation; for example, walking will most likely produce a shorter distance than driving. Nonetheless, similar relative behavior is observed between the compared schemes as with the time delay in comparison 800 (FIG. 8). It is important to further note that the small distances involved here, on the order of 30-40 meters, is close to the 10 m accuracy of GPS and at or below the known accuracy of cellular network trilateration.

Figure 10:
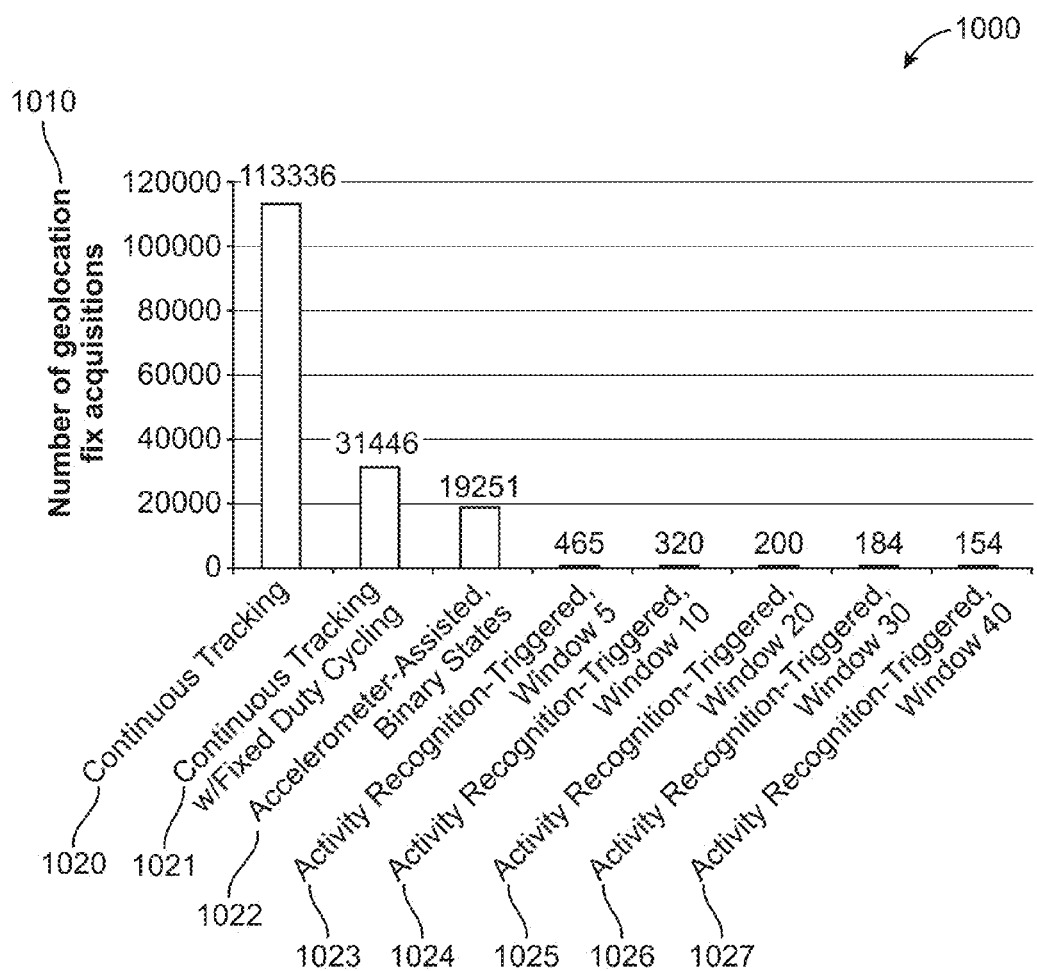
FIG. 10 shows an example comparison for different technologies for number of geolocation fix acquisitions, according to an embodiment.

FIG. 10 shows an example comparison 1000 for different technologies for number of geolocation fix acquisitions, according to an embodiment. In the comparison 1000, the number of geolocation fix acquisitions 1010 over the entire data set are shown for continuous tracking 1020, continuous tracking with fixed duty cycling 1021, accelerometer-assisted, binary states 1022, and embodiments comprising activity recognition-triggered window 5 1023, activity recognition-triggered window 10 1024, activity recognition-triggered window 20 1025, activity recognition-triggered window 30 1026 and activity recognition-triggered window 40 1027.

The core advantage offered by one or more embodiments is quantified with the comparison 1000. The comparison 1000 shows the number of geolocation fix acquisitions for each scheme over the entire data set. As expected, the continuous tracking 1020 and continuous tracking with fixed duty cycling 1021 schemes generate the most geolocation fixes, and even though the callbacks may be throttled as observed in earlier discussions, its total number is higher than the other schemes. The accelerometer-assisted, binary states 1022 scheme is more efficient, acquiring 5.9× fewer fixes than continuous tracking 1020 and 1.6× fewer than continuous tracking with fixed duty cycling 1021; its main advantage is that it disables geolocation fixes when the user is idle, such as when the user is sleeping. It can be seen that the activity recognition-triggered schemes are even more efficient and significantly reduces the number of geolocation fix acquisitions. With N=5 (activity recognition-triggered window 5 1023), the example embodiment produces 243× fewer fixes than continuous tracking 1020 and 41× fewer than accelerometer-assisted, binary states 1022.

The advantage of the example embodiments here stems from the intelligent transition-based triggering. Continuous tracking 1020 acquires geolocation fixes without regard for user events because it is missing the high-level information offered by sensor fusion, for example when coupled with an accelerometer. The accelerometer-assisted, binary states 1022 scheme improves upon continuous tracking 1020 scheme, but while it can eliminate geolocation fixes when the user is idle, it can neither distinguish with sufficient detail nor exploit the transition movements that humans emit.

Additionally, it can be observed that the longer windows for the activity recognition-triggered embodiments reduce the number of geolocation fixes. A longer window provides more smoothing over the raw activity stream produced by the classifier, reducing choppiness and spurious transitions due to mixed user activities. Note, however, that this smoothing and its apparent reduction in fix acquisitions cause longer delays and reduce recall (due to more missed events). Nonetheless, it is noted that the N=40 (activity recognition-triggered window 40 1027) configuration triggered 3× fewer fixes than the N=5 (activity recognition-triggered window 5 1023) configuration. All the schemes require that the CPU be active, and in the absence of a precise power-consumption model the number of geolocation fix acquisition are relied on as a close proxy for power usage.

Figure 11:
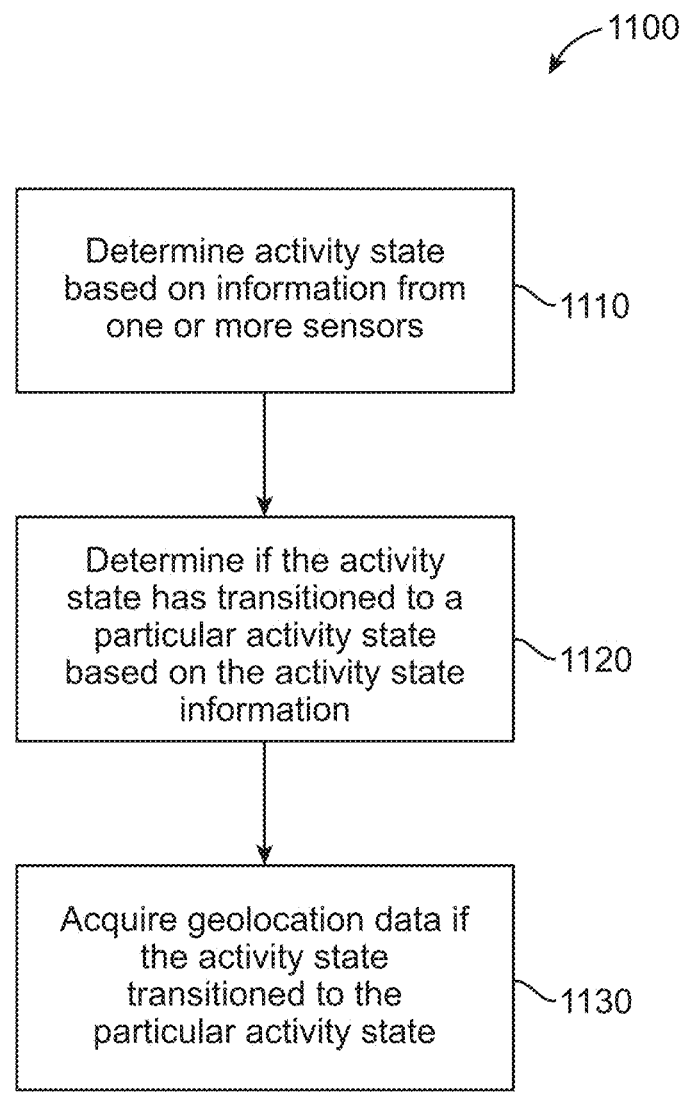
FIG. 11 shows a block diagram of an example process, according to one embodiment.

FIG. 11 shows a block diagram of an example process 1100, according to one embodiment. In one embodiment, in block 1110 activity state information is determined based on information from one or more sensors (e.g., accelerometer sensor(s)) 131 of an electronic device 120, FIG. 2). In block 1120, it is determined if an activity state has transitioned to a particular activity state based on the activity state information (e.g., transition from idle to driving, driving to walking, etc.). In block 1130 geolocation fix information is acquired if the activity state transitioned to the particular activity state.

One embodiment may include determining activity state information based on: determining tri-axis normalization on the acceleration data, extracting a sliding window based on the tri-axis normalization, obtaining magnitude of a frequency response based on the sliding window and computing features from time-domain information and frequency-domain information based on the magnitude of the frequency response. The process 1100 may further include concatenating features from the tri-axis information for obtaining a feature vector, and providing one or more of a trainer and classifier for recognizing activity states.

In one example, the tri-axis information comprises Cartesian magnitude information, true horizontal information and true vertical information. In another example, the trainer comprises a supervised machine learning trainer that provides offline training for providing mapping to physical activity states using a classification model, and the classifier provides classification of sensor data using information from the classification model for recognizing a plurality of activities.

In one embodiment, process 100 may include providing information (e.g., a reminder, an advertisement, etc.) to an electronic device based on the geolocation fix information. In one example, the geolocation fix information may include GPS information, Wi-Fi information or triangulation information. In another example, acquiring the geolocation fix information comprises controlling an active state of a GPS sensor or service.

In one example, the activity state information includes an indication of one or more moving and stationary activities. The moving activities comprise one or more of walking, running, driving, bicycling, flying, boating, and transporting, and the stationary activities comprise one or more of sitting, standing, and idling. In one embodiment, the process 100 may include determining if an activity state has transitioned to the particular activity state by transitioning between particular pairs of activity states (e.g., driving and idle).

Figure 12:
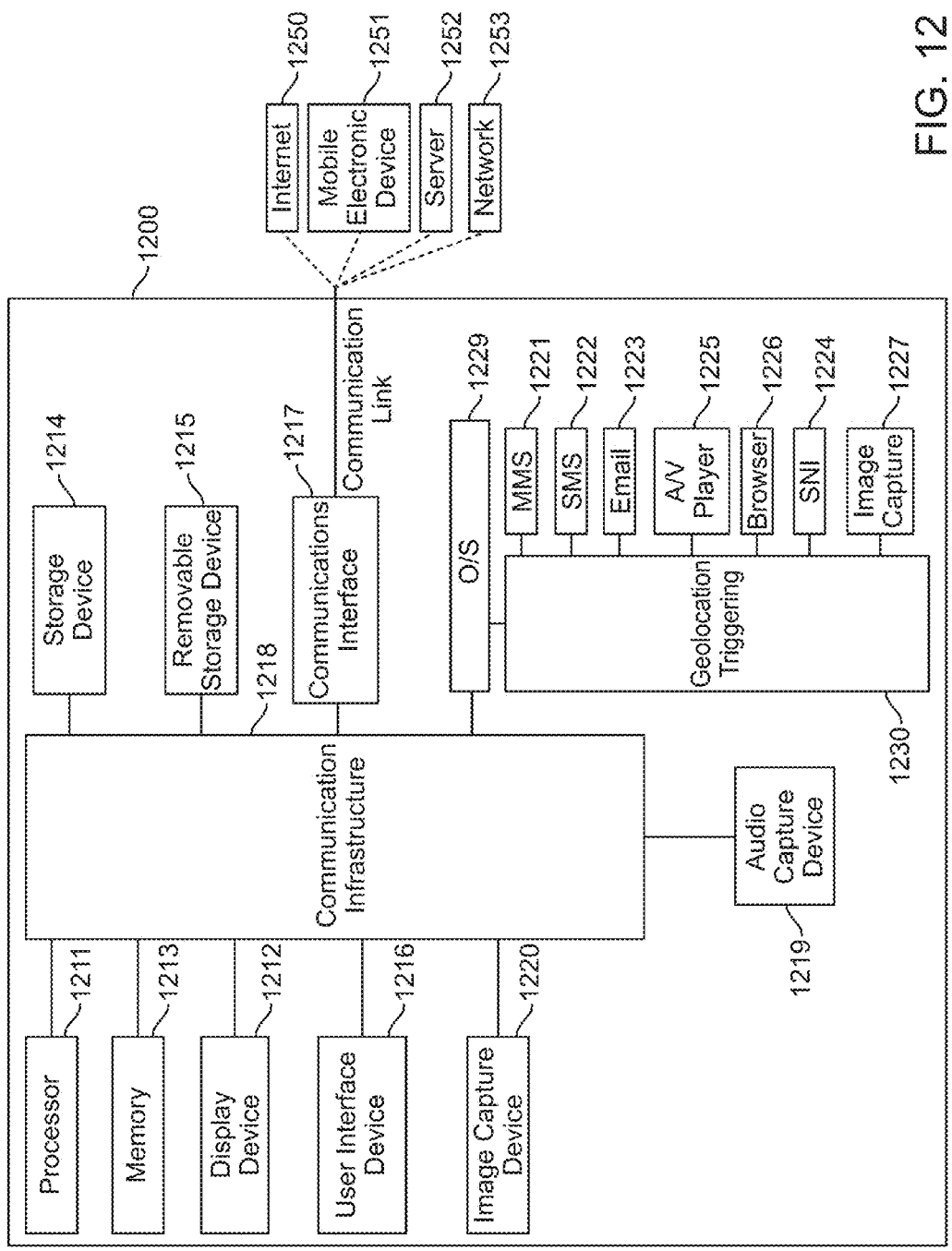
FIG. 12 is a high-level block diagram showing an information processing system comprising a computing system implementing one or more embodiments.

FIG. 12 is a high-level block diagram showing an information processing system comprising a computing system 1200 implementing one or more embodiments. The system 1200 includes one or more processors 1211 (e.g., ASIC, CPU, etc.), and may further include an electronic display device 1212 (for displaying graphics, text, and other data), a main memory 1213 (e.g., random access memory (RAM), cache devices, etc.), storage device 1214 (e.g., hard disk drive), removable storage device 1215 (e.g., removable storage drive, removable memory module, a magnetic tape drive, optical disk drive, computer-readable medium having stored therein computer software and/or data), user interface device 1216 (e.g., keyboard, touch screen, keypad, pointing device), and a communication interface 1217 (e.g., modem, wireless transceiver (such as Wi-Fi, Cellular), a network interface (such as an Ethernet card), a communications port, or a PCMCIA slot and card).

The communication interface 1217 allows software and data to be transferred between the computer system and external devices through the Internet 1250, mobile electronic device 1251, a server 1252, a network 1253, etc. The system 1200 further includes a communications infrastructure 1218 (e.g., a communications bus, cross bar, or network) to which the aforementioned devices/modules 1211 through 1217 are connected.

The information transferred via communications interface 1217 may be in the form of signals such as electronic, electromagnetic, optical, or other signals capable of being received by communications interface 1217, via a communication link that carries signals and may be implemented using wire or cable, fiber optics, a phone line, a cellular phone link, an radio frequency (RF) link, and/or other communication channels.

In one implementation of one or more embodiments in a mobile wireless device (e.g., a mobile phone, smartphone, tablet, mobile computing device, wearable device, etc.), the system 1200 further includes an image capture device 1220, such as a camera 128 (FIG. 2), and an audio capture device 1219, such as a microphone 122 (FIG. 2). The system 1200 may further include application modules as MMS module 1221, SMS module 1222, email module 1223, social network interface (SNI) module 1224, audio/video (AV) player 1225, web browser 1226, image capture module 1227, etc.

In one embodiment, the system 1200 includes a geolocation triggering module 1230 that may implement system 300 processing similar as described regarding (FIG. 3), and components in block diagram 100 (FIG. 2). In one embodiment, the geolocation triggering module 1230 may implement the system 300 (FIG. 3), and 400 (FIG. 4) and flow diagrams 600 (FIG. 6), 700 (FIG. 7) and 1100 (FIG. 11). In one embodiment, the geolocation triggering module 1230 along with an operating system 1229 may be implemented as executable code residing in a memory of the system 1200. In another embodiment, the geolocation triggering module 1230 may be provided in hardware, firmware, etc.

As is known to those skilled in the art, the aforementioned example architectures described above, according to said architectures, can be implemented in many ways, such as program instructions for execution by a processor, as software modules, microcode, as computer program product on computer readable media, as analog/logic circuits, as application specific integrated circuits, as firmware, as consumer electronic devices, AV devices, wireless/wired transmitters, wireless/wired receivers, networks, multi-media devices, etc. Further, embodiments of said Architecture can take the form of an entirely hardware embodiment, an entirely software embodiment or an embodiment containing both hardware and software elements.

One or more embodiments have been described with reference to flowchart illustrations and/or block diagrams of methods, apparatus (systems) and computer program products according to one or more embodiments. Each block of such illustrations/diagrams, or combinations thereof, can be implemented by computer program instructions. The computer program instructions when provided to a processor produce a machine, such that the instructions, which execute via the processor create means for implementing the functions/operations specified in the flowchart and/or block diagram. Each block in the flowchart/block diagrams may represent a hardware and/or software module or logic, implementing one or more embodiments. In alternative implementations, the functions noted in the blocks may occur out of the order noted in the figures, concurrently, etc.

The terms "computer program medium," "computer usable medium," "computer readable medium", and "computer program product," are used to generally refer to media such as main memory, secondary memory, removable storage drive, a hard disk installed in hard disk drive. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Computer program instructions may be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Computer program instructions representing the block diagram and/or flowcharts herein may be loaded onto a computer, programmable data processing apparatus, or processing devices to cause a series of operations performed thereon to produce a computer implemented process. Computer programs (i.e., computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system. A computer program product comprises a tangible storage medium readable by a computer system and storing instructions for execution by the computer system for performing a method of one or more embodiments.

Though the embodiments have been described with reference to certain versions thereof; however, other versions are possible. Therefore, the spirit and scope of the appended claims should not be limited to the description of the preferred versions contained herein.

What is claimed is:

1. A method for triggering acquisition of geolocation fix information comprising:
    obtaining sensor information from at least one sensor;
    determining, using the sensor information, activity state information based on:
        determining normalization information on the sensor information;
        extracting a sliding window based on the normalization information; and
        computing features from time-domain information and frequency-domain information based on a magnitude of a frequency response obtained based on the sliding window;
    determining whether an activity state has transitioned between particular activity states based on the activity state information; and
    triggering geolocation fix information based on a determination that activity state transitions between the particular activity states.

2. The method of claim 1, wherein the sensor comprises at least one accelerometer sensor, and the sensor information comprises acceleration data acquired from the at least one accelerometer sensor.

3. The method of claim 2, wherein:
    the normalization information comprises tri-axis normalization information on the acceleration data; and
    the sliding window is extracted based on the tri-axis normalization information.

4. The method of claim 3, further comprising:
    concatenating features from the tri-axis normalization information for obtaining a feature vector; and
    providing at least one of a trainer and classifier for recognizing activity states.

5. The method of claim 4, wherein the tri-axis normalization information comprises Cartesian magnitude information, true horizontal information and true vertical information.

6. The method of claim 5, wherein the trainer comprises a supervised machine learning trainer that provides offline training for providing mapping to physical activity states using a classification model, and the classifier provides classification of sensor data using information from the classification model for recognizing a plurality of activities.

7. The method of claim 6, further comprising providing information to an electronic device based on the geolocation fix information.

8. The method of claim 1, wherein the geolocation fix information comprises at least one of global positioning system information, Wi-Fi information, and triangulation information.

9. The method of claim 1, wherein acquisition of the geolocation fix information comprises controlling an active state of a global positioning system sensor.

10. The method of claim 1, wherein the activity state information comprises an indication of at least one of a moving activity and a stationary activity.

11. The method of claim 10, wherein the moving activity comprises at least one of walking, running, driving, bicycling, flying, boating, and transporting, and the stationary activity comprises at least one of sitting, standing, and idling.

12. The method of claim 11, wherein determining whether an activity state has transitioned between the particular activity states comprises determining the activity state transitions between particular pairs of activity states.

13. The method of claim 2, wherein the electronic device comprises at least one of a smart phone, a tablet device, a portable computing device, a wearable device and a camera device.

14. An electronic device comprising:
    at least one sensor configured to provide sensed data;
    an activity recognizer configured to determine, using the sensed data, activity state information based on:
        determining normalization information on the sensed data;
        extracting a sliding window based on the normalization information; and
        computing features from time-domain information and frequency-domain information based on a magnitude of a frequency response obtained based on the sliding window;
    a transition manager configured to determine whether an activity state has transitioned between particular activity states based on the activity state information; and
    a geolocation service or geolocation sensor configured to trigger acquisition of geolocation fix information upon a determination that the activity state transitions between the particular activity states.

15. The electronic device of claim 14, wherein the at least one sensor comprises at least one accelerometer sensor that is configured to provide the sensed data.

16. The electronic device of claim 14, wherein:
    the normalization information comprises tri axis normalization information; and
    the sliding window is extracted based on the tri-axis normalization information.

17. The electronic device of claim 16, further comprising a smoother configured to concatenate features from the tri-axis information to obtain a feature vector, wherein the tri-axis normalization information comprises Cartesian magnitude information, true horizontal information and true vertical information.

18. The electronic device of claim 17, further comprising a supervised machine learning trainer configured to provide offline training to provide mapping to physical activity states using a classification model, and wherein the activity recognizer includes a classifier that is configured to classify the sensed data using information from the classification model to recognize a plurality of activities.

19. The electronic device of claim 18, wherein a geolocation based application is configured to provide information to the electronic device based on the geolocation fix information.

20. The electronic device of claim 14, wherein the geolocation fix information comprises at least one of global positioning system information, Wi-Fi information, and triangulation information.

21. The electronic device of claim 14, wherein the transition manager is configured to control an active state of a global positioning system sensor.

22. The electronic device of claim 14, wherein the activity state information comprises an indication of at least one of a moving activity and a stationary activity, and the moving activity comprises at least one of walking, running, driving, bicycling, flying, boating, and transporting, and the stationary activity comprises at least one of sitting, standing, and idling.

23. The electronic device of claim 14, wherein the transition manager is configured to determine whether an activity state has transitioned between the particular activity states based on a transition between particular pairs of activity states.

24. The electronic device of claim 14, further comprising at least one of a smart phone, a tablet device, a portable computing device, a wearable device and a camera device.

25. A non-transitory processor-readable medium that includes a program that when executed by a processor performs a method comprising:
 obtaining sensed data from at least one sensor;
 determining, using the sensed data, activity state information based on:
  determining normalization information on the sensed data;
  extracting a sliding window based on the normalization information; and
  computing features from time-domain information and frequency-domain information based on a magnitude of a frequency response obtained based on the sliding window;
 determining whether an activity state has transitioned between particular activity states based on the activity state information; and
 triggering acquisition of geolocation fix information based on a determination that activity state transitions between the particular activity states.

26. The non-transitory processor-readable medium of claim 25, wherein the program that when executed by a processor performs a method further comprising providing information to an electronic device based on the geolocation fix information, and the geolocation fix information comprises at least one of global positioning system information, Wi-Fi information, and triangulation information.

27. The non-transitory processor-readable medium of claim 26, wherein the electronic device comprises at least one of a smart phone, a tablet device, a portable computing device, a wearable device and a camera device.

28. The non-transitory processor-readable medium of claim 25, wherein acquisition of the geolocation fix information comprises controlling an active state of a global positioning system sensor, and the activity state information comprises an indication of at least one of a moving activity and a stationary activity.

29. The non-transitory processor-readable medium of claim 28, wherein the moving activity comprises at least one of walking, running, driving, bicycling, flying, boating, and transporting, and the stationary activity comprises at least one of sitting, standing, and idling.

30. The non-transitory processor-readable medium of claim 29, wherein determining whether an activity state has transitioned between the particular activity states comprises determining transitions between particular pairs of activity states.

* * * * *